United States Patent
Latimer et al.

[11] Patent Number: 6,158,285
[45] Date of Patent: *Dec. 12, 2000

[54] EMAT INSPECTION OF WELDS IN THIN STEEL PLATES OF DISSIMILAR THICKNESSES

[75] Inventors: Paul J. Latimer; Daniel T. MacLauchlan, both of Lynchburg, Va.

[73] Assignee: McDermott Technology, Inc., New Orleans, La.

[*] Notice: This patent issued on a continued prosecution application filed under 37 CFR 1.53(d), and is subject to the twenty year patent term provisions of 35 U.S.C. 154(a)(2).

[21] Appl. No.: 08/918,292

[22] Filed: Aug. 26, 1997

[51] Int. Cl.[7] ................................................. G01N 29/10
[52] U.S. Cl. .......................... 73/643; 73/598; 73/600; 73/627
[58] Field of Search .............................. 73/598, 600, 643, 73/627, 629, 618, 620, 633, 622; 228/9, 5.7, 56.5

[56] References Cited

U.S. PATENT DOCUMENTS

| | | | |
|---|---|---|---|
| 3,868,847 | 3/1975 | Gunkel | 73/625 |
| 4,100,809 | 7/1978 | Bobrov et al. | 73/643 |
| 4,144,766 | 3/1979 | Wehrmeister | 73/587 |
| 4,593,568 | 6/1986 | Telford et al. | 73/629 |
| 5,085,082 | 2/1992 | Cantor et al. | 73/643 |
| 5,439,157 | 8/1995 | Geier et al. | 73/643 |
| 5,537,876 | 7/1996 | Davidson et al. | 73/643 |
| 5,760,307 | 6/1998 | Latimer et al. | 73/643 |
| 5,866,820 | 2/1999 | Camplin et al. | 73/643 |

*Primary Examiner*—Helen C. Kwok
*Attorney, Agent, or Firm*—R. J. Edwards; Eric Marich; R. C. Baraona

[57] ABSTRACT

A method for inspecting welds uses a single EMAT tranducer operated in pulse-echo mode that sends and receives Rayleigh waves to detect defects in a weld between sheet plates of dissimilar thicknesses.

5 Claims, 1 Drawing Sheet

EMAT INSPECTION OF WELDS IN THIN STEEL PLATES OF DISSIMILAR THICKNESSES

FIELD AND BACKGROUND OF THE INVENTION

The present invention relates in general to the inspection of welds, and in particular to a new and useful inspection technique which utilizes an Electromagnetic Acoustic Transducer or EMAT.

Laser welded panels are used in such applications as automobile doors where variations in thickness are desirable in a component to reduce material costs and weight. Many welding defects are encountered in the welding mismatch such as lack of fusion, lack of penetration, concavity, and step mismatch. The current method for detecting these defects is by visual inspection. This method is both slow and ineffective since many defects cannot be identified by visual techniques.

SUMMARY OF THE INVENTION

An object of the present invention is to provide a technique that uses surface wave EMATs to inspect laser welded blanks or other thin steel plates or similar material that have a dissimilar thickness and are welded together.

The problem of detecting a small flaw at the position of a step due to dissimilar thicknesses is difficult for conventional ultrasonic techniques because the large signal from the step makes it difficult to detect a small defect signal. In laser welded blanks, a thinner material is welded to a thicker sheet.

The basis of the present technique is the use of pulse-echo Rayleigh waves to avoid a response due to the step resulting from the dissimilar thickness step in the weld. Since the plates are thin, it is necessary to insure that Lamb wave modes are not excited since Lamb waves would produce a reflection at the step. It is observed, both theoretically and experimentally, that the thickness must be approximately four times the wavelength to insure that only Rayleigh waves are excited. A neodymium iron permanent magnet is used since a significant number of the plates needed to verify the invention were galvanized and the use of pulsed magnets would not be efficient due to the lack of magnetostriction in the zinc coating. A focused EMAT is used to improve resolution of small defects. A natural defect consisting of a half through-wall pinhole exhibited a signal to noise ratio that was great enough to allow it to be used as a calibration standard.

Accordingly, an object of the present invention is to provide a method for inspecting a weld between thin plates, comprising: using an electromagnetic acoustic transducer to generate Rayleigh waves; focusing the Rayleigh waves toward the weld to create echo Rayleigh waves which are reflected from the weld; receiving the echo Rayleigh waves in the transducer to create electrical detection signals; and analyzing the electrical detection signals to identify a defect in the weld.

A further object of the present invention is to utilize a selected frequency for the focused Rayleigh waves which depends on the thickness of the thin steel plates which are welded to each other.

A still further object of the present invention is to scan the focused Rayleigh waves across the weld at a rate of about 20 ips (inches per second).

A still further object of the present invention is to provide an apparatus for the EMAT inspection of welds in the thin sheet plates, in particular welded plates which are of dissimilar thicknesses.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
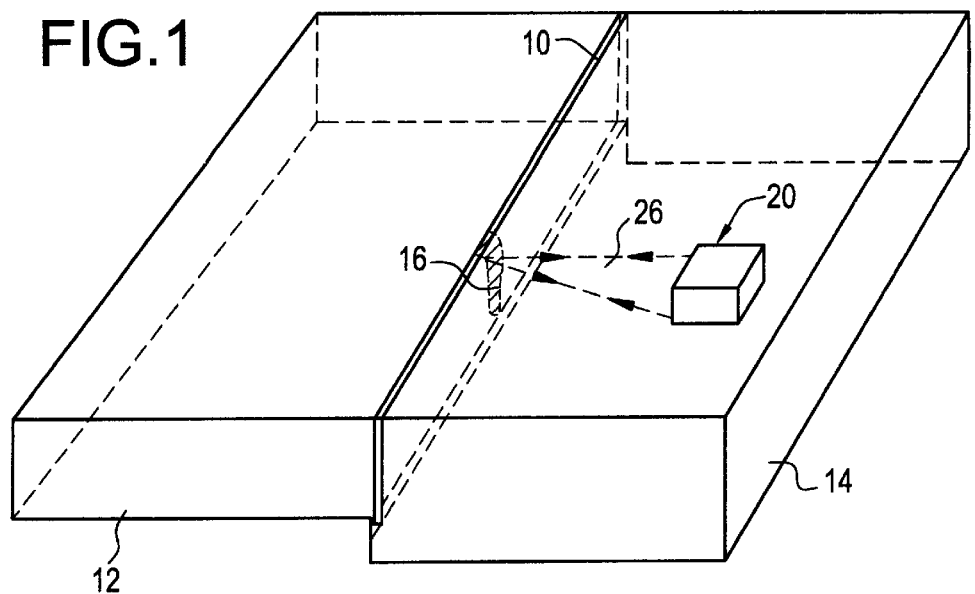
FIG. 1 is a schematic perspective view of a weld between thin steel plates of dissimilar thicknesses which is to be inspected according to the present invention.

Referring to the drawings in particular, the invention embodied in FIG. 1 comprises a method and apparatus for inspecting a weld 10 in thin steel plates, in particular welds between plates 12 and 14 of dissimilar thicknesses.

Figure 2:
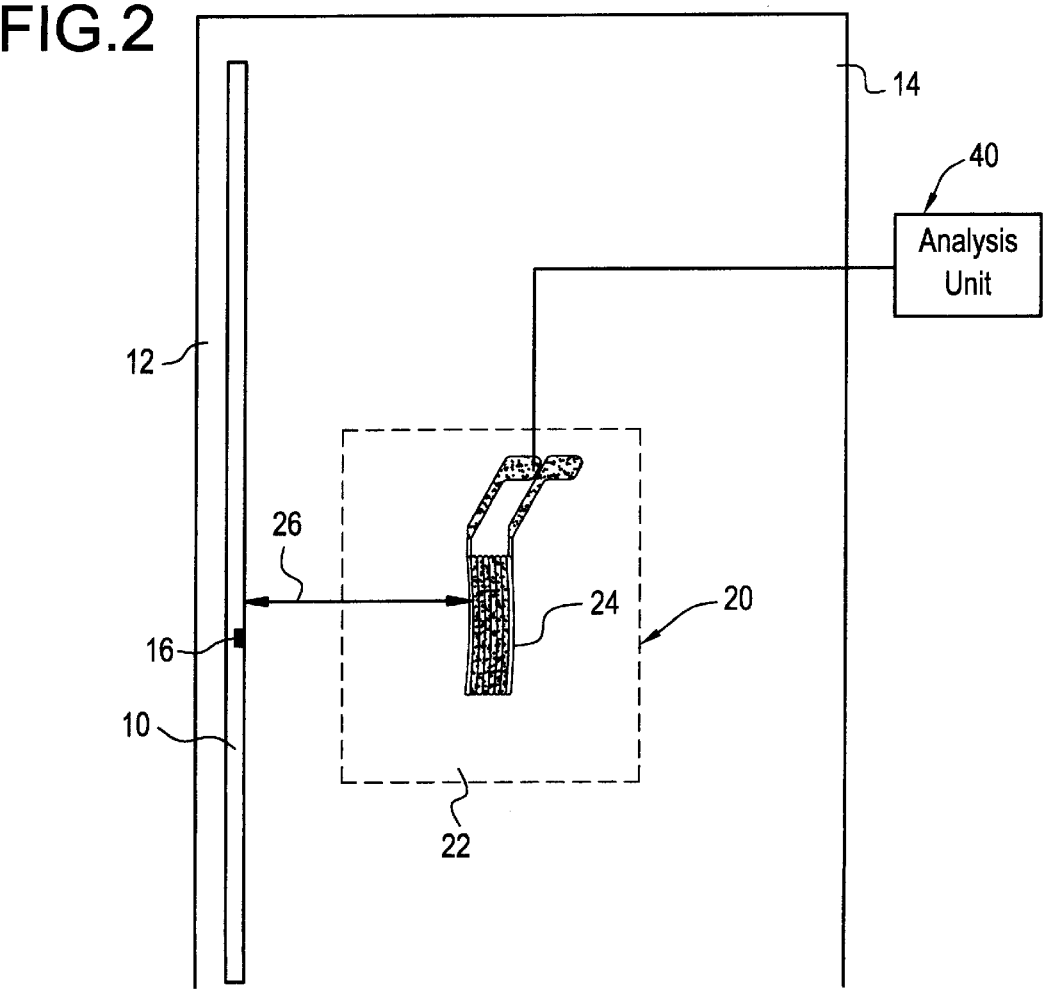
FIG. 2 is a top plan view of the EMAT sensor of the present invention adjacent the weld to be inspected.

The invention utilizes an EMAT transducer or sensor generally designated 20 in FIGS. 1 and 2, which, as shown in FIG. 2, comprises a magnet 22 and an EMAT coil 24. Sensor 20 is moved across an outer surface of one of the plates with the coil 24 oriented to generate a focused Rayleigh wave toward the weld 10, along the focal axis 26 of the EMAT coil 24 in the embodiment of FIG. 2, a focal length along focal axis 26 of about 1.83 inches is selected. A length of 1–2 inches or more is preferred. EMAT coil 24 is designed to both generate the focused Rayleigh wave impulses and also to receive echo Rayleigh waves back from weld 10, along the axis or focal area 26 as shown in FIG. 1. An analysis unit generally designated 40 is connected to coil 24 and is of known design and construction for analyzing the echo Rayleigh waves from the EMAT coil 24. These waves can be used to generate graphs and other graphic displays which change to indicate the condition of the weld 10, and in particular to detect the presence of defects. In order to verify the effectiveness of the present invention, weld 10 was provided with a defect 16 in the form of a half through-wall pinhole 16.

By using EMAT 20 in pulse-echo mode as a surface wave sensor, a single EMAT is sufficient. Scanning is always performed from the thicker side of the steel plate; for example, the upper surface of plate 14 in FIG. 1. This insures that the Rayleigh surface waves are excited instead of Lamb wave modes and plate modes which would generate a step response. A titanium wear plate on the surface of magnet 22 facing plate 14 was used to protect the EMAT coil 24 from slivers and other imperfections which may damage the EMAT coil 24. Unit 40 is a standard computer controlled tone burst system developed by The Babcock & Wilcox Company.

The results of laboratory investigations indicate that the present system operating at a frequency of 6 MHz can resolve a half through-wall pinhole (surface opening of 0.42" and depth of 0.034") with a scanning speed of 20 ips. The system can resolve pin holes, lack of fusion, skip arcing, and lack of penetration with a depth of 0.005". In addition, the requirement for weld location away from the transducer was plus or minus 0.7" which were considerably wider and thus better than the 0.25" requirement in the original industry specification.

At a frequency of 6 MHz, the inventive system was able to inspect blanks which had a plate with a thickness of 0.073" or greater. It is recommended that an 8 MHz sensor by used for inspection of blanks whose thicker component is 0.060" or greater. A 12 Mhz sensor is recommended for blanks whose thicker component is within the range from 0.035" to 0.059". All samples supplied were successfully inspected at 6 MHz except for one that had a thickness of 0.064". The inspection was performed with available equipment and the 0.064" plate would require fabrication of 8 MHz surface wave EMAT coils.

The EMAT instrument is the standard computer controlled tone burst system developed by The Babcock & Wilcox Company. The Temate® scan software developed by Innerspec® Technologies was used for both instrumentation control and data acquisition. A B-scan presentation was chosen for data display because it is readily adaptable to rapid automated scanning.

Advantages of the invention include:
a) The technique described represents a significant improvement in defect detection over the use of visual techniques that are now being employed.
b) The technique can scan at twice the rate specified by the industry.
c) Weld location away from the transducer was much wider and thus better than industry specifications.
d) The visual appearance of defects in the B-scans are easily interpreted and require minimum operator training.
e) The technique works equally well with both galvanized and non-galvanized materials.
f) This inspection method is ideal for an automated environment.
g) The method requires no fluid to couple the sound into the part being tested.

The techniques described in this disclosure are not restricted to laser welded blanks. The techniques are applicable to thin conductive sheets of dissimilar thickness or the same thickness, that are joined by any welding process.

While specific embodiments of the invention have been shown and described in detail to illustrate the application of the principles of the invention, it will be understood that the invention may be embodied otherwise without departing from such principles.

What is claimed is:

1. A method for detecting small defects in a weld between two thin plates wherein one of the plates is thicker than the other plate, the thicker plate having an upper surface and the thinner plate having a measurable thickness, comprising:

placing an electromagnetic acoustic transducer (EMAT) along the upper surface of the thicker plate at a set distance from the weld, the EMAT including an EMAT coil having a focal axis;

using the EMAT to exclusively generate Rayleigh waves to penetrate the weld having a wavelength that is greater than one quarter of the thickness of the thinner plate;

orienting the EMAT coil so that the focal axis is perpendicular to the weld and sending the Rayleigh waves toward the weld to create echo Rayleigh waves which are reflected from the weld;

receiving the echo Rayleigh waves in the EMAT to create electrical detection signals; and analyzing the electrical detection signals to identify a defect in the weld.

2. A method according to claim 1, further comprising:
selecting and operating the EMAT at a frequency based upon a plate thickness of the thicker one of the plates welded together.

3. A method according to claim 2, wherein the selected frequency is 6 MHz and the plate thickness is 0.073" or greater.

4. A method according to claim 2, wherein the selected frequency is 12 MHz and the plate thickness is between 0.035" and 0.059".

5. A method according to claim 1, wherein the set distance is between one and two inches from the surface of the weld on the upper surface of the thicker plate.

* * * * *